US009241939B2

(12) United States Patent
Garcia-Echeverria et al.

(10) Patent No.: US 9,241,939 B2
(45) Date of Patent: Jan. 26, 2016

(54) COMBINATION OF (A) A PHOSPHOINOSITIDE 3-KINASE INHIBITOR AND (B) A MODULATOR OF RAS/RAF/MEK PATHWAY (71) Applicants: Carlos Garcia-Echeverria, Saint-Cloud (FR); Sauveur-Michel Maira, Habsheim (FR); Darrin Stuart, Pleasant Hill, CA (US); Susan Wee, Skillman, NJ (US); Christine Fritsch, Steinbach (FR); Tobi Nagel, Oakland, CA (US)

(72) Inventors: Carlos Garcia-Echeverria, Saint-Cloud (FR); Sauveur-Michel Maira, Habsheim (FR); Darrin Stuart, Pleasant Hill, CA (US); Susan Wee, Skillman, NJ (US); Christine Fritsch, Steinbach (FR); Tobi Nagel, Oakland, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/576,314

(22) Filed: Dec. 19, 2014

(65) Prior Publication Data
US 2015/0105417 A1 Apr. 16, 2015

Related U.S. Application Data (60) Continuation of application No. 14/066,734, filed on Oct. 30, 2013, which is a division of application No. 13/003,581, filed as application No. PCT/US2009/050192 on Jul. 10, 2009, now abandoned.

(30) Foreign Application Priority Data

Jul. 11, 2008 (EP) ..................................... 08160218

(51) Int. Cl.
*A61K 31/497* (2006.01)
*A61K 31/4745* (2006.01)
*A61K 31/4188* (2006.01)
*A61K 45/06* (2006.01)
*A61K 31/166* (2006.01)
*A61K 31/437* (2006.01)
*A61K 31/4439* (2006.01)
*A61K 31/5377* (2006.01)

(52) U.S. Cl.
CPC ........... *A61K 31/4745* (2013.01); *A61K 31/166* (2013.01); *A61K 31/4188* (2013.01); *A61K 31/437* (2013.01); *A61K 31/4439* (2013.01); *A61K 31/5377* (2013.01); *A61K 45/06* (2013.01)

(58) Field of Classification Search
USPC .................................................. 514/253, 293
See application file for complete search history.

(56) References Cited

U.S. PATENT DOCUMENTS

| 2004/0116710 A1 | 6/2004 | Wallace |
| 2006/0014768 A1* | 1/2006 | Kawasaki et al. ............. 514/269 |
| 2011/0105521 A1 | 5/2011 | Garcia-Echeverria |

FOREIGN PATENT DOCUMENTS

| RU | 2192861 C1 | 11/2002 |
| WO | WO03/007914 A1 | 9/2003 |
| WO | WO2006/122806 | 11/2006 |
| WO | WO2007/030377 | 3/2007 |
| WO | WO2007/044084 A2 | 4/2007 |
| WO | WO2007/084786 | 7/2007 |
| WO | WO 2007/084786 * | 7/2007 |
| WO | WO2008/032162 | 3/2008 |
| WO | WO2010/029082 A1 | 3/2010 |
| WO | WO2011/054620 A1 | 5/2011 |

OTHER PUBLICATIONS

International Search Report for application PCT/US2009/050192 dated Apr. 11, 2009.
Nishioka C. et al: "ZD6474 induce growth arrest and apoptosis of human leukemia cells, which is enchanced by concomitant use of a novel MEK inhibitor, AZD6244", Leukemia (2007) 21, 1308-1310.
Shelton John G. et al: "Ability of the activated PI3K/Akt . . . ", Cell Cycle 3:4, 503-512; Apr. 2004.
Chiu Doris et al: "Acute activation of Erk1/Erk2 and protein . . . ", FEBS Journal 272 (2005) 4372-4384.
Handbook. Anticancer Therapy. Ed.by Perevodchikova N.I. M., Medicine 1993 pp. 8-9, first paragraph.
DACTOLISIB (CID 11977753) abstract [on-line] [found Apr. 2, 2013] (Found in PubChem; Create data Jan. 3, 2007).
SB590885 (CID 11316960) abstract [on-line] [found Apr. 2, 2013] (Found in PubChem; Create data Oct. 26, 2006).
RAF265 (CID 11656518) abstract [on-line] [found Apr. 2, 2013] (Found in PubChem; Create data Oct. 27, 2006).
Revill et al: "AZD06244 MEK ½ inhibitor oncolytic", Drugs of the Future, 2006, 31(10); 854-858.

* cited by examiner

*Primary Examiner* — Marcos Sznaidman
(74) *Attorney, Agent, or Firm* — Sandra Rueck (57) ABSTRACT The invention relates to a pharmaceutical combination which comprises (a) a phosphoinositide 3-kinase inhibitor compound and (b) a compound which modulates the Ras/Raf/Mek pathway for the treatment of a proliferative disease, especially a solid tumor disease; a pharmaceutical composition comprising such a combination; the use of such a combination for the preparation of a medicament for the treatment of a proliferative disease; a commercial package or product comprising such a combination as a combined preparation for simultaneous, separate or sequential use; and to a method of treatment of a warm-blooded animal, especially a human.

4 Claims, 6 Drawing Sheets

COMBINATION OF (A) A PHOSPHOINOSITIDE 3-KINASE INHIBITOR AND (B) A MODULATOR OF RAS/RAF/MEK PATHWAY

This is a continuation of U.S. patent application Ser. No. 14/066,734 filed on Oct. 30, 2013, which is a divisional of U.S. patent application Ser. No. 13/003,581 filed on Jan. 11, 2011, now abandoned, which is a National Stage of International Application No. PCT/US2009/0950192 filed on Jul. 10, 2009, which claims the benefit of European Patent Application No. EP 08160218.7, filed Jul. 11, 2008, which in its entirety are herein incorporated by reference.

The invention relates to a pharmaceutical combination which comprises (a) a phosphoinositide 3-kinase (PI3K) inhibitor compound and (b) a compound which modulates the Ras/Raf/Mek pathway and optionally at least one pharmaceutically acceptable carrier for simultaneous, separate or sequential use, in particular for the treatment of a proliferative disease, especially a proliferative disease in which the Ras/Raf/MeK and PI3K/Akt pathways are concomitantly dysregulated; a pharmaceutical composition comprising such a combination; the use of such a combination for the preparation of a medicament for the treatment of a proliferative disease; a commercial package or product comprising such a combination as a combined preparation for simultaneous, separate or sequential use; and to a method of treatment of a warm-blooded animal, especially a human.

WO2006/122806 describes imidazoquinoline derivatives, which have been described to inhibit the activity of lipid kinases, such as PI3-kinases. Specific imidazoquinoline derivatives which are suitable for the present invention, their preparation and suitable pharmaceutical formulations containing the same are described in WO2006/122806 and include compounds of formula I

(I)

wherein
R$_1$ is naphthyl or phenyl wherein said phenyl is substituted by one or two substituents independently selected from the group consisting of Halogen; lower alkyl unsubstituted or substituted by halogen, cyano, imidazolyl or triazolyl; cycloalkyl; amino substituted by one or two substituents independently selected from the group consisting of lower alkyl, lower alkyl sulfonyl, lower alkoxy and lower alkoxy lower alkylamino; piperazinyl unsubstituted or substituted by one or two substituents independently selected from the group consisting of lower alkyl and lower alkyl sulfonyl; 2-oxopyrrolidinyl; lower alkoxy lower alkyl; imidazolyl; pyrazolyl; and triazolyl;
R$_2$ is O or S;
R$_3$ is lower alkyl;
R$_4$ is pyridyl unsubstituted or substituted by halogen, cyano, lower alkyl, lower alkoxy or piperazinyl unsubstituted or substituted by lower alkyl; pyrimidinyl unsubstituted or substituted by lower alkoxy; quinolinyl unsubstituted or substituted by halogen; quinoxalinyl; or phenyl substituted with alkoxy
R$_5$ is hydrogen or halogen;
n is 0 or 1;
R$_6$ is oxido;
with the proviso that if n=1, the N-atom bearing the radical R$_6$ has a positive charge;
R$_7$ is hydrogen or amino;
or a tautomer thereof, or a pharmaceutically acceptable salt, or a hydrate or solvate thereof.

The radicals and symbols as used in the definition of a compound of formula I have the meanings as disclosed in WO2006/122806 which publication is hereby incorporated into the present application by reference.

A preferred compound of the present invention is a compound which is specifically described in WO2006/122806. A very preferred compound of the present invention is 2-methyl-2-[4-(3-methyl-2-oxo-8-quinolin-3-yl-2,3-dihydro-imidazo[4,5-c]quinolin-1-yl)-phenyl]-propionitrile and its monotosylate salt (COMPOUND A). The synthesis of 2-methyl-2-[4-(3-methyl-2-oxo-8-quinolin-3-yl-2,3-dihydro-imidazo[4,5-c]quinolin-1-yl)-phenyl]-propionitrile is for instance described in WO2006/122806 as Example 1. Another very preferred compound of the present invention is 8-(6-methoxy-pyridin-3-yl)-3-methyl-1-(4-piperazin-1-yl-3-trifluoromethyl-phenyl)-1,3-dihydro-imidazo[4,5-c]quinolin-2-one (COMPOUND B). The synthesis of 8-(6-methoxy-pyridin-3-yl)-3-methyl-1-(4-piperazin-1-yl-3-trifluoromethyl-phenyl)-1,3-dihydro-imidazo[4,5-c]quinolin-2-one is for instance described in WO2006/122806 as Example 86.

WO07/084786 describes pyrimidine derivatives, which have been found the activity of lipid kinases, such as PI3-kinases. Specific pyrimidine derivatives which are suitable for the present invention, their preparation and suitable pharmaceutical formulations containing the same are described in WO07/084786 and include compounds of formula I

II or a stereoisomer, tautomer, or pharmaceutically acceptable salt thereof, wherein,
W is CR$_w$ or N, wherein R$_w$ is selected from the group consisting of
(1) hydrogen,
(2) cyano,
(3) halogen,
(4) methyl,
(5) trifluoromethyl,
(6) sulfonamido;
R$_1$ is selected from the group consisting of
(1) hydrogen,
(2) cyano, (3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(22) —$SO_2R_{1a}$, and
(23) —$SO_2NR_{1a}R_{1b}$,
wherein $R_{1a}$ and $R_{1b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$,
wherein $R_{2a}$ and $R_{2b}$ are independently selected from the group consisting of
(a) hydrogen, and
(b) substituted or unsubstituted alkyl;
$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$, wherein $R_{3a}$ and $R_{3b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
$R_4$ is selected from the group consisting of
(1) hydrogen, and
(2) halogen.

The radicals and symbols as used in the definition of a compound of formula I have the meanings as disclosed in WO07/084786 which publication is hereby incorporated into the present application by reference.

A preferred compound of the present invention is a compound which is specifically described in WO07/084786. A very preferred compound of the present invention is 5-(2,6-di-morpholin-4-yl-pyrimidin-4-yl)-4-trifluoromethyl-pyridin-2-ylamine (COMPOUND C). The synthesis of 5-(2,6-di-morpholin-4-yl-pyrimidin-4-yl)-4-trifluoromethyl-pyridin-2-ylamine is described in WO07/084786 as Example 10.

The Ras/Raf/Mek signal transduction pathway is activated through the initial extracellular binding and stimulation of RTKs by their respective cognate ligands. Upon autophosphorylation of specific tyrosine residues in the cytosolic domain of RTKs, the Grb2-Sos complex translocates to the plasma membrane, and converts the inactive Ras.GDP to active Ras.GTP. The interaction between Grb2 and the activated kinases or the phosphorylated receptor associated proteins is mediated by the SH2 domain of the signalling protein that recognizes specific phosphotyrosine sequences. Ras undergoes a conformational changes upon GTP binding and causes the recruitment of Raf-1 to the cytoplasmic membrane where is phosphorylated by several kinases and simultaneous disphosphorylated at key residues by protein phosphatase-2B. Activated Raf phosphorylates Mek on two serine residues in the activation loop, which results in the activation of this protein kinase. Mek then phosphorylates and activates Erk, allowing its translocation to the nucleus where it phosphorylates transcriptional factors permitting the expression of a variety of genes. As shown in this section, several components of the Raf/Mek/Erk cascade represent unique opportunities for cancer treatment, e.g. genetic alterations such as HRAS, KRAS, NRAS or BRAF mutations or gene amplifications.

Sorafenib, also known as Nexavar™ or BAY 43-9006, has been the first Raf kinase modulator to receive marketing approval for treatment of advanced renal cell carcinoma (RCC). Sorafenib is a bi-aryl urea derivative of the following structure:

Sorafenib and methods for its preparation have been described e.g. in U.S. Pat. No. 7,235,576 or U.S. Pat. No. 7,351,834.

RAF265 (previously known as CHIR-265) is another orally bioavailable Raf modulator of following structure:

RAF265 and methods for its preparation for are for instance described in WO07/030377.

Further Raf kinase modulators include for instance SB590885, XL281, PLX4032.

Mek kinase modulators include compounds described in WO02/06213, in particular compound PD-0325901 which has following structure:

Another related Mek kinase inhibitor is compound PD-181461.

Further Mek kinase modulators include compounds described in WO03/077914, in particular compound ARRY142886/AZD6244 of structure and ARRY-509 and the compounds described in WO05/051906, WO05/023251, WO03/077855 and US20050049419 covering N3-alkylated benzimidazoles and other similar heterocyclic derivatives as MEK inhibitors for the treatment of hyperproliferative diseases.

Further Mek kinase modulators include for instance XL518, JTP-74057, AS-701255, AS-701173.

Hence, the present invention also pertains to a combination such as a combined preparation or a pharmaceutical composition which comprises (a) a phosphoinositide 3-kinase (PI3K) inhibitor compound and (b) a compound which modulates the Ras/Raf/Mek pathway. More particularly, in a first embodiment, the present invention relates to a combination which comprises (a) a phosphoinositide 3-kinase (PI3K) inhibitor compound and (b) a Raf kinase modulator or Mek kinase modulator.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g. in order to cope with the needs of a patient sub-population to be treated or the needs of the single.

It has been found that combination therapy with an PI3K inhibitor and a raf-kinase or mek-kinase inhibitor results in unexpected improvement in the treatment of tumor diseases. When administered simultaneously, sequentially or separately, the PI3K inhibitor and the raf-kinase or mek-kinase inhibitor interact in a synergistic manner to inhibit cell proliferation. This unexpected synergy allows a reduction in the dose required of each compound, leading to a reduction in the side effects and enhancement of the clinical effectiveness of the compounds and treatment.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between tumor models and effects seen in man suggest that synergy in animals may e.g. be demonstrated in the BN472 tumor model or pancreatic PANC1 and MiaPaCa2 tumor models as described in the Examples below.

In one aspect the present invention provides a synergistic combination for human administration comprising (a) PI3K inhibitor compound and (b) a compound which modulates the Ras/Raf/Mek pathway, or pharmaceutically acceptable salts or solvates thereof, in a combination range (w/w) which corresponds to the ranges observed in a tumor model, e.g. as described in the Examples below, used to identify a synergistic interaction. Suitably, the ratio range in humans corresponds to a non-human range selected from between 50:1 to 1:50 parts by weight, 50:1 to 1:20, 50:1 to 1:10, 50:1 to 1:1, 20:1 to 1:50, 20:1 to 1:20, 20:1 to 1:10, 20:1 to 1:1, 10:1 to 1:50, 10:1 to 1:20, 10:1 to 1:10, 10:1 to 1:1, 1:1 to 1:50, 1.1 to 1:20 and 1:1 to 1:10. More suitably, the human range corresponds to a non-human range of the order of 10:1 to 1:1 or 5:1 to 1:1 or 2:1 to 1:1 parts by weight.

According to a further aspect, the present invention provides a synergistic combination for administration to humans comprising an (a) a PI3K inhibitor compound and (b) a compound which modulates the Ras/Raf/Mek pathway or pharmaceutically acceptable salts thereof, where the dose range of each component corresponds to the synergistic ranges observed in a suitable tumor model, e.g. the tumor models described in the Examples below, primarily used to identify a synergistic interaction. Suitably, the dose range of the PI3K inhibitor compound in human corresponds to a dose range of 1-50 mg/kg, more suitably 1-30 mg/kg (e.g. 1-35 mg/kg or 1-10 mg/kg for Compound A, 1-25 mg/kg for Compound B) in a suitable tumor model, e.g. a rat or mouse model as described in the Examples below.

For the compound which modulates the Ras/Raf/Mek pathway, the dose range in the human suitably corresponds to a synergistic range of 1-50 mg/kg or 1-30 mg/kg (e.g. 1-25 mg/kg, 1-10 mg/kg or 1-2.5 mg/kg) in a suitable tumor model, e.g. a rat or mouse model as described in the Examples below.

Suitably, the dose of PI3K inhibitor compound for use in a human is in a range selected from 1-1200 mg, 1-500 mg, 1-100 mg, 1-50 mg, 1-25 mg, 500-1200 mg, 100-1200 mg, 100-500 mg, 50-1200 mg, 50-500 mg, or 50-100 mg, suitably 50-100 mg, once daily or twice daily (b.i.d.) or three times per day (t.i.d.), and the dose of compound which modulates the Ras/Raf/Mek pathway is in a range selected from 1-1000 mg, 1-500 mg, 1-200 mg, 1-100 mg, 1-50 mg, 1-25 mg, 10-100 mg, 10-200 mg, 50-200 mg or 100-500 mg once daily, b.i.d or t.i.d.

In accordance with a further aspect the present invention provides a synergistic combination for administration to humans comprising an (a) a PI3K inhibitor compound at 10%-100%, preferably 50%-100% or more preferably 70%-100%, 80%-100% or 90%-100% of the maximal tolerable dose (MTD) and (b) a compound which modulates the Ras/Raf/Mek pathway at 10%-100%, preferably 50%-100% or more preferably 70%-100%, 80%-100% or 90%-100% of the MTD. In a preferred embodiment one of the compounds, preferably the PI3K inhibitor compound, is dosed at the MTD and the other compound, preferably the compound which modulates the Ras/Raf/Mek pathway, is dosed at 50%-100% of the MTD, preferably at 60%-90% of the MTD. The MTD corresponds to the highest dose of a medicine that can be given without unacceptable side effects. It is within the art to determine the MTD.

For instance the MTD can suitably be determined in a Phase I study including a dose escalation to characterize dose limiting toxicities and determination of biologically active tolerated dose level.

In one embodiment of the invention, (a) the phosphoinositide 3-kinase (PI3K) inhibitor compound inhibitor is selected from the group consisting of COMPOUND A, COMPOUND B or COMPOUND C.

In one embodiment of the invention, (b) the Raf kinase modulator is selected from the group consisting of Sorafenib, Raf265, SB590885, XL281 and PLX4032. In another embodiment, (b) the Mek kinase modulator is selected from the group consisting of PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 and AS703026.

The term "treating" or "treatment" as used herein comprises the a treatment effecting a delay of progression of a disease. The term "delay of progression" as used herein means administration of the combination to patients being in a pre-stage or in an early phase of the proliferative disease to be treated, in which patients for example a pre-form of the corresponding disease is diagnosed or which patients are in a condition, e.g. during a medical treatment or a condition resulting from an accident, under which it is likely that a corresponding disease will develop.

In one embodiment of the present invention, the proliferative disease is melanoma, lung cancer, colorectal cancer (CRC), breast cancer, kidney cancer such as e.g. renal cell carcinoma (RCC), liver cancer, acute myelogenous leukemia (AML), myelodysplastic Syndromes (MDS), non-small-cell lung cancer (NSCLC), thyroid cancer, pancreatic cancer, neurofibromatosis or hepatocellular carcinoma.

In another embodiment of the present invention, the proliferative disease is a solid tumor. The term "solid tumor" especially means breast cancer, ovarian cancer, cancer of the colon and generally the GI (gastro-intestinal) tract, cervix cancer, lung cancer, in particular small-cell lung cancer, and non-small-cell lung cancer, head and neck cancer, bladder cancer, cancer of the prostate or Kaposi's sarcoma. The present combination inhibits the growth of solid tumors, but also liquid tumors. Furthermore, depending on the tumor type and the particular combination used a decrease of the tumor volume can be obtained. The combinations disclosed herein are also suited to prevent the metastatic spread of tumors and the growth or development of micrometastases. The combinations disclosed herein are in particular suitable for the treatment of poor prognosis patients, especially such poor prognosis patients having metastatic melanome or pancreatic cancer.

The cancer to be treated can have a genetic alteration in the Ras/Raf/Mek signal transduction pathway such as e.g. a HRAS, KRAS, NRAS or BRAF mutation or gene amplification. In one embodiment the cancer to be treated has a KRAS mutation, e.g. KRAS mutated pancreas cancer, colon cancer, lung cancer (e.g. NSCLC) or leukemias.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

It will be understood that references to the combination partners (a) and (b) are meant to also include the pharmaceutically acceptable salts. If these combination partners (a) and (b) have, for example, at least one basic center, they can form acid addition salts. Corresponding acid addition salts can also be formed having, if desired, an additionally present basic center. The combination partners (a) and (b) having an acid group (for example COOH) can also form salts with bases. The combination partner (a) or (b) or a pharmaceutically acceptable salt thereof may also be used in form of a hydrate or include other solvents used for crystallization.

A combination which comprises (a) a phosphoinositide 3-kinase inhibitor compound and (b) a compound which modulates the Ras/Raf/Mek pathway, in which the active ingredients are present in each case in free form or in the form of a pharmaceutically acceptable salt and optionally at least one pharmaceutically acceptable carrier, will be referred to hereinafter as a COMBINATION OF THE INVENTION.

The COMBINATION OF THE INVENTION are both synergistic and additive advantages, both for efficacy and safety. Therapeutic effects of combinations of a phosphoinositide 3-kinase inhibitor compound with a compound which modulates the Ras/Raf/Mek pathway can result in lower safe dosages ranges of each component in the combination.

The pharmacological activity of a COMBINATION OF THE INVENTION may, for example, be demonstrated in a clinical study or in a test procedure as essentially described hereinafter. Suitable clinical studies are, for example, open label non-randomized, dose escalation studies in patients with advanced solid tumors. Such studies can prove the additive or synergism of the active ingredients of the COMBINATIONS OF THE INVENTION. The beneficial effects on proliferative diseases can be determined directly through the results of these studies or by changes in the study design which are known as such to a person skilled in the art. Such studies are, in particular, suitable to compare the effects of a monotherapy using the active ingredients and a COMBINATION OF THE INVENTION. Preferably, the combination partner (a) is administered with a fixed dose and the dose of the combination partner (b) is escalated until the Maximum Tolerated Dosage is reached.

It is one objective of this invention to provide a pharmaceutical composition comprising a quantity, which is therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man. Alternatively, when the agents are administered separately, one can be an enteral formulation and the other can be administered parenterally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils, alcohols, flavoring agents, preservatives, coloring agents; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

In particular, a therapeutically effective amount of each of the combination partner of the COMBINATION OF THE INVENTION may be administered simultaneously or sequentially and in any order, and the components may be administered separately or as a fixed combination. For example, the method of delay of progression or treatment of a proliferative disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The COMBINATION OF THE INVENTION can be a combined preparation or a pharmaceutical composition.

Moreover, the present invention relates to a method of treating a warm-blooded animal having a proliferative disease comprising administering to the animal a COMBINATION OF THE INVENTION in a quantity which is therapeutically effective against said proliferative disease.

Furthermore, the present invention pertains to the use of a COMBINATION OF THE INVENTION for the treatment of a proliferative disease and for the preparation of a medicament for the treatment of a proliferative disease.

Moreover, the present invention provides a commercial package comprising as active ingredients COMBINATION OF THE INVENTION, together with instructions for simultaneous, separate or sequential use thereof in the delay of progression or treatment of a proliferative disease.

Preferred embodiments of the invention are represented by combinations comprising
  COMPOUND A, COMPOUND B or COMPOUND C and Sorafenib,
  COMPOUND A, COMPOUND B or COMPOUND C and RAF265

In another preferred embodiment, the invention provides combinations comprising
  COMPOUND A and Sorafenib, Raf265, SB590885, XL281 or PLX4032.
  COMPOUND B and Sorafenib, Raf265, SB590885, XL281 or PLX4032.
  COMPOUND C and Sorafenib, Raf265, SB590885, XL281 or PLX4032.
  COMPOUND A and PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.
  COMPOUND B and PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.
  COMPOUND C and PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.

In further aspects, the present inventions provides
  a combination which comprises (a) a COMBINATION OF THE INVENTION, wherein the active ingredients are present in each case in free form or in the form of a pharmaceutically acceptable salt or any hydrate thereof, and optionally at least one pharmaceutically acceptable carrier; for simultaneous, separate or sequential use;
  a pharmaceutical composition comprising a quantity which is jointly therapeutically effective against a proliferative disease of a COMBINATION OF THE INVENTION and at least one pharmaceutically acceptable carrier;
  the use of a COMBINATION OF THE INVENTION for the treatment of a proliferative disease;
  the use of a COMBINATION OF THE INVENTION for the preparation of a medicament for the treatment of a proliferative disease;

the use of a combination COMBINATION OF THE INVENTION wherein the PI3K inhibitor is selected from COMPOUND A, COMPOUND B or COMPOUND C;

the use of a COMBINATION OF THE INVENTION wherein the compound which modulates the Ras/Raf/Mek pathway is compound which modulates Raf kinase activity, e.g. Sorafenib, RAF265, SB590885, XL281, PLX4032; and the use of COMBINATION OF THE INVENTION wherein the compound which modulates the Ras/Raf/Mek pathway is a compound which modulates Mek kinase activity, e.g. PD-0325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.

Moreover, in particular, the present invention relates to a combined preparation, which comprises (a) one or more unit dosage forms of a phosphoinositide 3-kinase inhibitor compound and (b) a compound which modulates the Ras/Raf/Mek pathway.

Furthermore, in particular, the present invention pertains to the use of a combination comprising (a) a phosphoinositide 3-kinase inhibitor compound and (b) a compound which modulates the Ras/Raf/Mek pathway for the preparation of a medicament for the treatment of a proliferative disease.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

When the combination partners employed in the COMBINATION OF THE INVENTION are applied in the form as marketed as single drugs, their dosage and mode of administration can take place in accordance with the information provided on the package insert of the respective marketed drug in order to result in the beneficial effect described herein, if not mentioned herein otherwise.

COMPOUND A may be administered to a human in a dosage range varying from about 50 to 800 mg/day.

COMPOUND B may be administered to a human in a dosage range varying from about 25 to 800 mg/day.

COMPOUND C may be administered to a human in a dosage range varying from about 25 to 800 mg/day.

Sorafenib may be administered to a human in a dosage range varying from about 75 to 800 mg/day, more preferable 400 mg taken twice daily.

The following Examples illustrate the invention described above; they are not, however, intended to limit the scope of the invention in any way. The beneficial effects of the COMBINATION OF THE INVENTION can also be determined by other test models known as such to the person skilled in the pertinent art.

EXAMPLES

Example 1 the MEK inhibitor PD0325901 synergizes with compound A in an antiproliferative assay. The KRAS mutant NSCLC cell line was used in a standard methylene blue proliferation assay. In this assay, compound A and PD0325901 inhibited the proliferation with a G150 (that is the concentration for which 50% of growth inhibition is observed) of 9.41 and 36.8 nM respectively (Table 1). When tested in combination, the G150 for BEZ235 decrease to 3.2 nM, that is to say to say that in presence of PD0325901, 3 times less BEZ235 is required to observe a similar decrease in proliferation. Conversely, the G150 for PD0325901 decreased to 11.5 nM in presence of compound A. The combination Index obtained is of 0.718, which correspond to a moderate synergism (Table 2).

TABLE 1

| Compound | GI50 (in nM) alone | GI50 (in nM) in combination | Combination Index (CI) |
|---|---|---|---|
| Compound A | 9.41 | 4.46 | 0.718 |
| NVP-LBW624 | 36.8 | 11.5 | |

A549 cells were incubated with increasing amount of either compound A or PD0325901 (NVP-LBW624) alone or in combination, for 72 h and proliferation assessed with a standard methylene blue assay. The G150 were determined and CI quantified with the CalcuSyn software.

TABLE 2

| CI Value | Phenotypical response |
| --- | --- |
| 1.1 to 10 | antagonism |
| 0.9 to 1.1 | Nearly additive |
| 0.85 to 0.9 | Slight synergism |
| 0.7 to 0.85 | Moderate synergism |
| 0.3 to 0.7 | synergim |
| 0.1 to 0.3 | Strong synergism |

Figure 1:
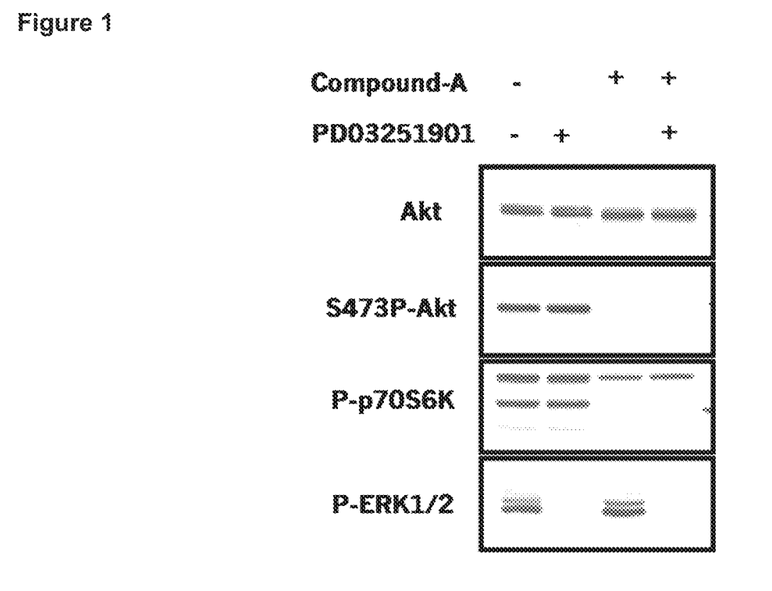
FIG. 1: A549 cells were incubated either with compound A, PD03251901 (250 nM) alone or in combination for 30 min. Cells were then harvested and estimation of phosphorylated levels of either Akt; p70S6K or ERK done by regular Western-blotting.

Example 2 the MEK inhibitor and compound A when incubated in cells alone do block their respective downstream effectors (ERK and Akt). When A549 cells are incubated in the presence of both inhibitors, then both pathway are effectively and simultaneously blocked (FIG. 1).

Example 3

Figure 2:
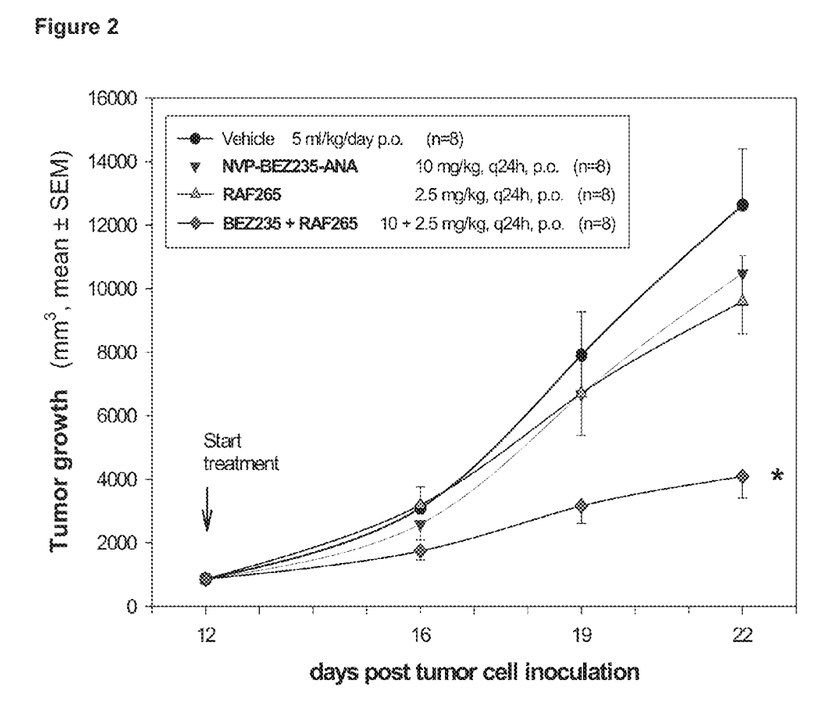
FIG. 2: Rat bearing BN472 tumors were treated with the indicated compound at the indicated dose and schedule, either alone or in combination. Evolution of tumor growth were followed by callipering throughout the course of the study. *, P<0.05 (Dunnett's).
Figure 3:
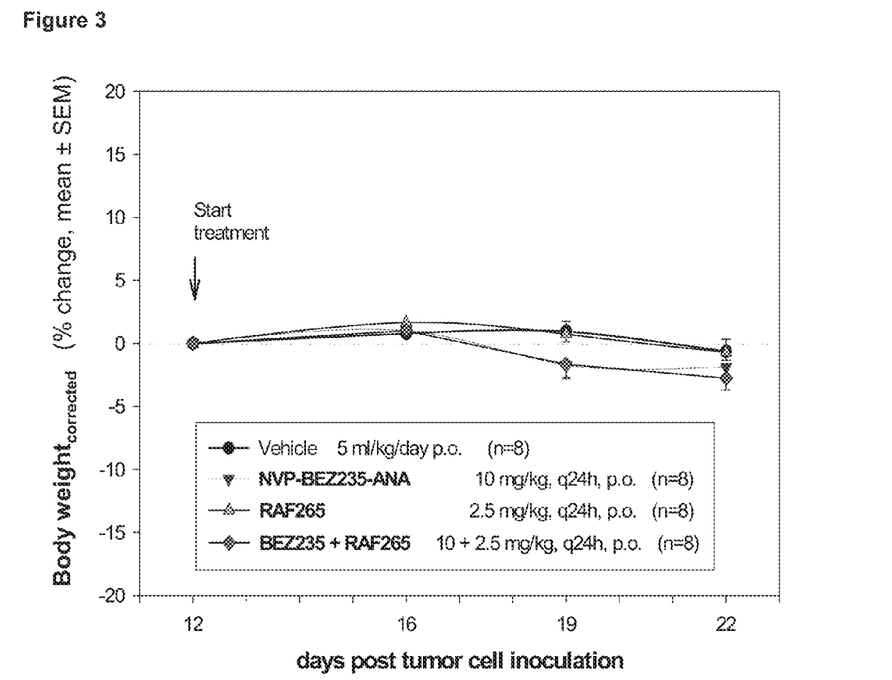
FIG. 3: Rat bearing BN472 tumors were treated with the indicated compound at the indicated dose and schedule, either alone or in combination. Evolution of body weight were followed throughout the course of the study. *, P<0.05 (Dunnett's).

In the BN472 tumor model administration of compound A at a dose of 10 mg/kg (p.o., 1q24h) or the Raf inhibitor Raf265 (at a dose of 2.5 mg/kg, po, &q24h) produced a weak and not significant antitumor activity (expressed as T/C) of either 83 and 76. The combination of compound A (10 mg/kg) with RAF265, however, produced a strong and statistically significant antitumor activity with a T/C of 34% (FIG. 2). The combination was well tolerated as no effect on body weight could be measured (FIG. 3).

Example 4

Figure 4:
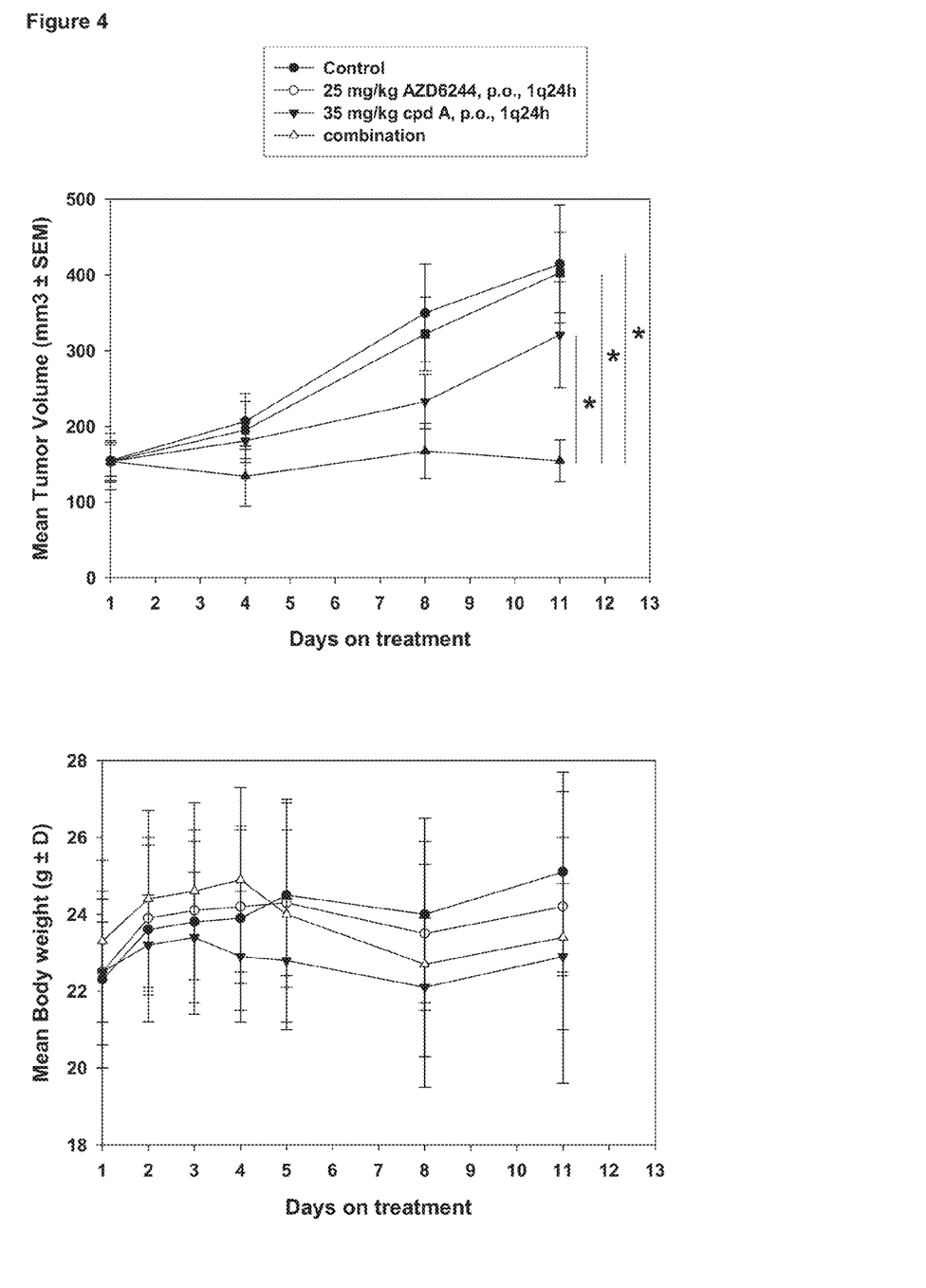
FIG. 4: KRAS mutant PANC1 cells were grown subcutaneously on the flank of Harlan nude mice and treated with either compound A, AZD6244 alone or in combination for 12 days. Evolutions of Tumor volume (A) and body weight (B) were measured throughout the course of the study. *, p<0.05 (Dunnett's).

KRAS mutant PANC1 cells were grown subcutaneously on the flank of Harlan nude mice. Tumor bearing animals were then treated with the indicated compounds and dosage regimen in FIG. 4. Evolutions of Tumor volume (A) and body weight (B) were measured throughout the course of the study, until day 12 at which time the animals were sacrificed. *, $p<0.05$, One way ANOVA followed by Tukey post hoc test, showing that the antitumor activity obtained in the combo group is significantly different from the control and single agent treated groups (synergistic activity between the two compounds).

Example 5

Figure 5:
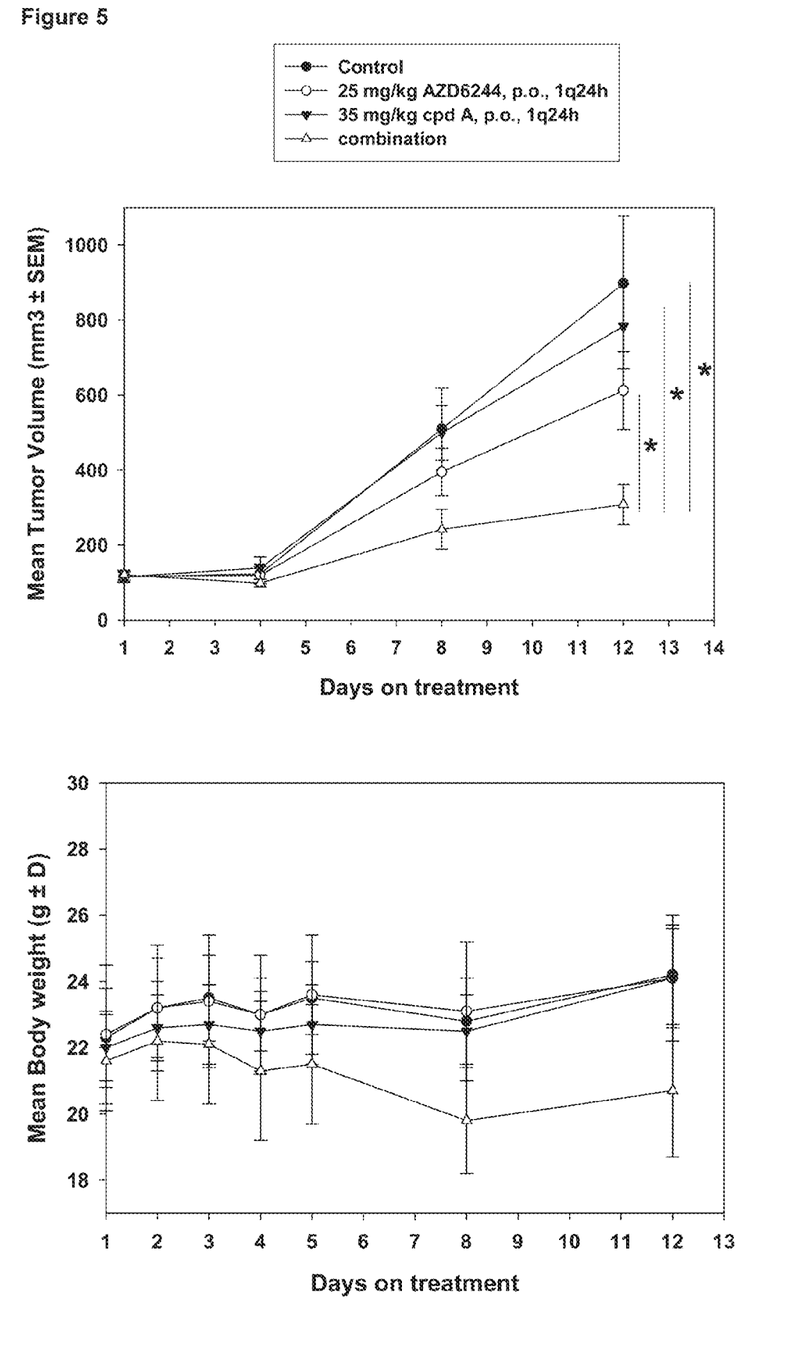
FIG. 5: KRAS mutant MiaPaCa2 cells were grown subcutaneously on the flank of Harlan nude mice and treated with either compound A, AZD6244 alone or in combination for 12 days. Evolutions of Tumor volume (A) and body weight (B) were measured throughout the course of the study. *, p<0.05 (Dunnett's).
Figure 6:
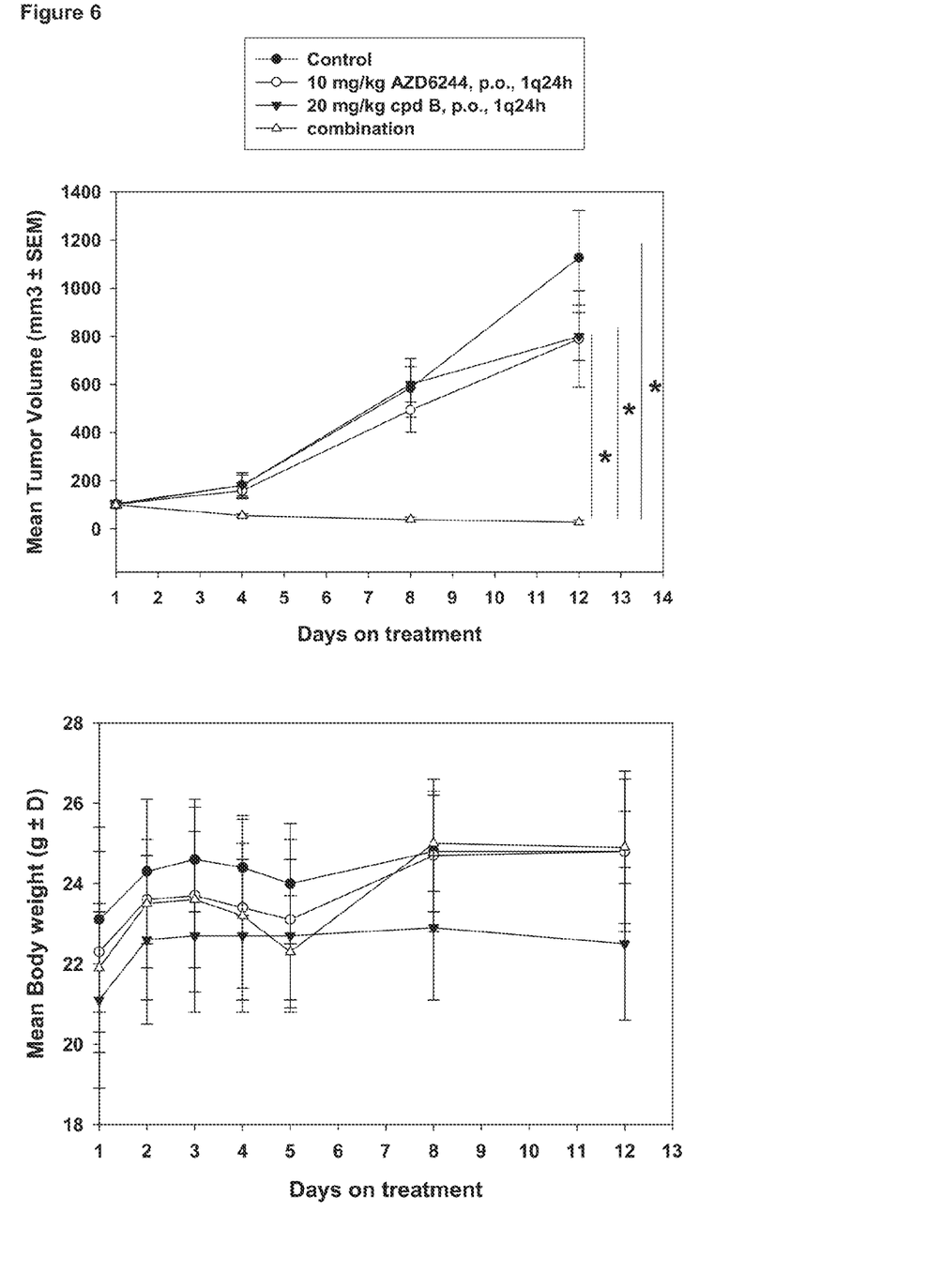
FIG. 6: KRAS mutant MiaPaCa2 cells were grown subcutaneously on the flank of Harlan nude mice and treated with either 5-(2,6-di-morpholin-4-yl-pyrimidin-4-yl)-4-trifluoromethyl-pyridin-2-ylamine (COMPOUND C, termed here cpd B), AZD6244 alone or in combination for 12 days. Evolutions of Tumor volume (A) and body weight (B) were measured throughout the course of the study. *, p<0.05 (Dunnett's).

KRAS mutant MiaPaCa2 cells were grown subcutaneously on the flank of Harlan nude mice. Tumor bearing animals were then treated with the indicated compounds and dosage regimen in FIGS. 5 and 6. Evolutions of Tumor volume (A) and body weight (B) were measured throughout the course of the study, until day 12 at which time the animals were sacrificed. *, $p<0.05$, One way ANOVA followed by Tukey post hoc test, showing that the antitumor activity obtained in the combo group is significantly different from the control and single agent treated groups (synergistic activity between the two compounds).

What is claimed is:

1. A method of treating a warm-blooded animal having a pancreatic cancer, comprising simultaneously, sequentially or separately administering to said animal (a) a phosphoinositide 3-kinase inhibitor compound selected from 5-(2,6-di-morpholin-4-yl-pyrimidin-4-yl)-4-trifluoromethyl-pyridin-2-ylamine and (b) a compound which modulates Mek kinase activity selected from ARRY142886/AZD6244, ARRY162, and GSK1120212, wherein the active ingredients are present in free form or in the form of a pharmaceutically acceptable salt thereof, in a quantity which is therapeutically effective against said proliferative disease.

2. A method according to claim 1, wherein the compound which modulates Mek kinase activity is ARRY162, or GSK1120212 or a pharmaceutically acceptable salt thereof.

3. A method according to claim 1, wherein the pancreatic cancer has a genetic alteration in the Ras/Raf/Mek signal transduction pathway consisting of a HRAS, KRAS, NRAS or BRAF mutation or gene amplification.

4. A method of treating a warm-blooded animal having a pancreatic cancer, comprising administering to said animal (a) a phosphoinositide 3-kinase inhibitor compound 5-(2,6-di-morpholin-4-yl-pyrimidin-4-yl)-4-trifluoromethyl-pyridin-2-ylamine and (b) a compound GSK1120212, wherein the active ingredients are present in free form or in the form of a pharmaceutically acceptable salt thereof, in a quantity which is therapeutically effective against said pancreatic cancer.

* * * * *